(12) United States Patent
Schmitz

(10) Patent No.: US 11,925,427 B2
(45) Date of Patent: Mar. 12, 2024

(54) BIOMETRICALLY SCALABLE AI DESIGNED ARTICULATED CATHETER DEVICE

(71) Applicant: Gregory P. Schmitz, Los Gatos, CA (US)

(72) Inventor: Gregory P. Schmitz, Los Gatos, CA (US)

( * ) Notice: Subject to any disclaimer, the term of this patent is extended or adjusted under 35 U.S.C. 154(b) by 0 days.

(21) Appl. No.: 18/186,176

(22) Filed: Mar. 19, 2023

(65) Prior Publication Data

US 2023/0225811 A1 Jul. 20, 2023

Related U.S. Application Data

(60) Continuation-in-part of application No. 17/318,617, filed on May 12, 2021, now abandoned, which is a division of application No. 16/270,714, filed on Feb. 8, 2019, now Pat. No. 11,033,342.

(60) Provisional application No. 62/632,031, filed on Feb. 19, 2018.

(51) Int. Cl.
*A61B 34/30* (2016.01)
*A61B 34/00* (2016.01)
*H02K 15/00* (2006.01)

(52) U.S. Cl.
CPC ............ *A61B 34/30* (2016.02); *H02K 15/00* (2013.01); *A61B 2034/306* (2016.02); *A61B 2034/715* (2016.02)

(58) Field of Classification Search
None
See application file for complete search history.

(56) References Cited

U.S. PATENT DOCUMENTS

| | | | |
|---|---|---|---|
| 10,029,072 B2 | 7/2018 | Hebert et al. | |
| 2002/0019660 A1* | 2/2002 | Gianotti | A61F 2/915 623/1.15 |
| 2006/0184232 A1* | 8/2006 | Gianotti | A61F 2/91 623/1.15 |
| 2007/0135803 A1* | 6/2007 | Belson | A61B 1/00154 606/1 |
| 2012/0143173 A1 | 6/2012 | Steege et al. | |

(Continued)

*Primary Examiner* — Mohammad Ali
*Assistant Examiner* — David Earl Ogg
(74) *Attorney, Agent, or Firm* — Stephen E. Zweig

(57) ABSTRACT

Computerized system and method of manufacturing an articulated surgical device. Surgical device pathway data (often from medical scans), target and entry point location data, and design parameters in computer memory are used to automatically design, and subsequently manufacture the customized device. The device typically comprises a plurality of units, which may have varying lengths and widths, connected to other units by at least one moveable joint. The device is configured to accommodate multiple pull cables, often running from the distal to the proximal end. These cables enable an operator, often using a proximal control device, to precisely control the orientation of the distal end as the device traverses a patient's body pathways. The distal end of the device may have an effector unit configured to perform a medical task. Design and manufacture are facilitated by use of AI computerized design methods and computer controlled (CNC, laser cutting, 3D printing) methods.

20 Claims, 11 Drawing Sheets

(56) References Cited

U.S. PATENT DOCUMENTS

2015/0265849 A1* 9/2015 Krechting .............. A61B 34/10
                                                    264/129
2017/0095922 A1* 4/2017 Licht ...................... A61B 34/76

* cited by examiner

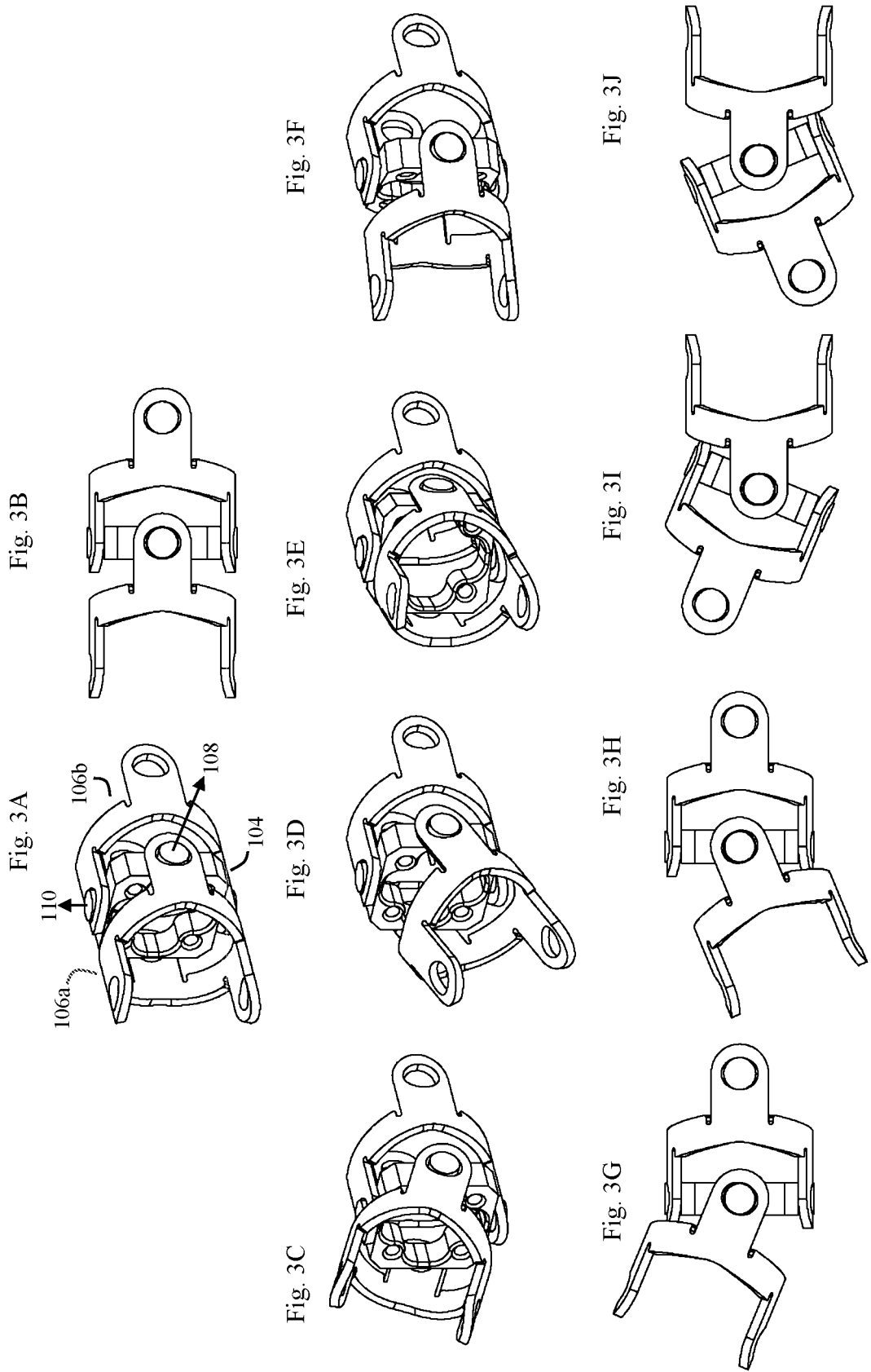

BIOMETRICALLY SCALABLE AI DESIGNED ARTICULATED CATHETER DEVICE

CROSS REFERENCE TO RELATED APPLICATIONS

This invention is a continuation in part of U.S. patent application Ser. No. 17/318,617; application Ser. No. 17/318,617 was a division of U.S. patent application Ser. No. 16/270,714, filed Feb. 8, 2019, now U.S. Pat. No. 11,033,342, issued Jun. 15, 2021; application Ser. No. 16/270,714 claimed the priority benefit of U.S. provisional patent application 62/632,031, filed Feb. 19, 2018; the entire contents of these disclosures are incorporated herein by reference.

BACKGROUND OF THE INVENTION

Field of the Invention

This invention is in the field of medical catheters, medical robotics, and medical robotic catheters.

Description of the Related Art

Catheters are widely used in many aspects of surgery and medicine. These include cardiac catheters configured to be inserted at an opening in one of the patient's veins, which are then guided to a target region in the heart. Such catheters have often tipped with various types of effector devices configured to administer therapeutic drugs or radiological contrast agents, apply stents, balloon devices, and the like.

Laparoscopic surgery has also become popular in recent years. Often called keyhole surgery, such methods aim to minimize patient trauma by the use of small thin surgical tools that can enter the body through small incisions, and then perform useful surgical work. Towards this end, many ingenious devices have been devised, including various types of laparoscopes and other surgical tools. Robotic surgery, exemplified by Intuitive Surgical's Da Vinci Robotic-Assisted Surgery platform, also employs sophisticated robotic control methods for performing laparoscopic and other types of keyhole surgery.

Catheters often comprise a single "snake" or "hose" like structure that has no or almost no internal joints, and thus are not "articulated." Many classical laparoscopic devices have a middle section that is often straight, and thus is not articulated at least in this middle section as well. In-between these two extremes is a third class of elongated device comprised of a large number of smaller jointed units, all strung together in a manner not unlike a necklace. If properly controlled, such articulated devices offer the promise of working on medical problems where traditional catheter designs and laparoscopes have difficulties addressing.

One example of an articulated surgical device is Kalbe et. al, U.S. Pat. No. 10,029,073. Kalbe taught a type of steerable assembly for a surgical catheter. This was an articulated device comprised of multiple units, which Kalbe called segments. Each unit is a self-sufficient link connected to another unit by a joint allowing pivoting about a single axis between the different units (links).

As another example, Schmitz (also the inventor of the present application), in U.S. Pat. No. 11,033,342, disclosed an articulated device called a universal joint for surgical robotics. This articulated device was also comprised of multiple units. but here each unit further comprised a link and yoke configured so that each unit was connected to another unit by multiple joints allowing pivoting about a double axis between the units.

FIG. 1A shows an example of an articulated surgical device (100). In this embodiment, the device is made up of repeating articulated units (102), where each unit comprises a yoke (104) and a link (106), and each unit is able to rotate about two independent axes (108) and (110). These are sometimes referred to in this disclosure as "hypermobile" units.

FIG. 1B shows an alternate example of an articulated surgical device (120), in this alternative embodiment, the device is also made up of repeating articulated units (122), where each unit comprises only link (126), and each link is able to rotate about only one axis (124). Thus in FIG. 1B, unit (122) and link (126) are the same.

BRIEF SUMMARY OF THE INVENTION

The invention was inspired, in part, by the insight that articulated medical devices, such as the previously discussed Kalbe and Schmitz devices, can have a superior ability to areas of the body that are presently difficult to access using prior art catheter and laparoscope designs.

The invention was also inspired, in part, by the insight that there is a wide variation in patient morphology, particularly with regards to branching body lumens such as blood vessels, lung structures, certain intestinal regions, and the like. Although articulated medical devices, which can as needed be finely manipulated and guided through the use of internal pull wires, offer some advantages here, the wide variation in patient morphology makes it difficult for a standardized design to fit all situations.

The invention was also inspired, in part, by the insight that modern medical scanning methods, coupled with modern computer aided design techniques (often artificial intelligence assisted techniques), coupled with improvements in automated manufacturing methods now make it feasible to rapidly produce customized designs. Specifically, the invention is inspired by the concept of a system and method that can rapidly progress from medical scans to a customized articulated catheter or articulated laparoscopic device precisely customized to handle medical situations not well served by prior art devices.

Thus in some embodiments, the invention may be a computerized system and method of manufacturing an articulated surgical device. Expressed in methods terminology, this method can produce a customized device from surgical device pathway data (often obtained from medical scans) describing at least some structural dimensions of a patient's body lumen or other internal body passage. Other data, such as target location data describing at least one target location in said patient's body that is relative to this pathway, and the surgical device design parameters are also needed. Here assume that the articulated surgical device comprises a plurality of connected units, each with at least one moveable joint, which may have variable diameters or lengths.

The computerized system, usually comprising at least one computer processor and often specialized AI-type coprocessors, can take this data and automatically design a patient customized articulated surgical device which may be customized for that particular patient's body morphology and medical need. The output from this design may then be used, often in conjunction with suitable automated manufacturing processes such as laser cutting and/or CNC methods, to rapidly produce the customized device. Indeed, a range of customized devices, often configured to handle situations where standard catheters, endoscopes, bronchoscopes or laparoscopes have problems, can be manufactured in advance and kept on hand or in stock for emergency use.

BRIEF DESCRIPTION OF THE DRAWINGS

FIG. 3A-J show a detailed close up of a link, yoke, link (a unit and a half) from FIG. 1A. As can be seen, the link on the left is connected to the yoke by one yoke pivot boss, and the link on the right is connected to the yoke by a different yoke pivot boss, thus enabling a hypermobile series of units that can simultaneously swivel up and down, and from left to right as shown.

DETAILED DESCRIPTION OF THE INVENTION

As previously discussed, the invention is based, in part, on the insight that the utility of various types of articulated surgical devices can be enhanced if the devices are further customized for a given patient and a given set of surgical problems.

Figure 1A:
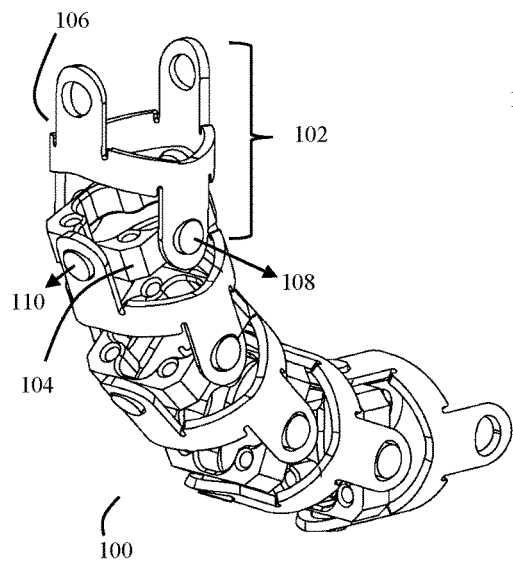
FIG. 1A shows an example of an articulated surgical device. In this embodiment, the device is made up of repeating articulated units, where each unit comprises a yoke and a link, and each unit is able to rotate about two independent axes. These are sometimes referred to as hypermobile units.
Figure 2:
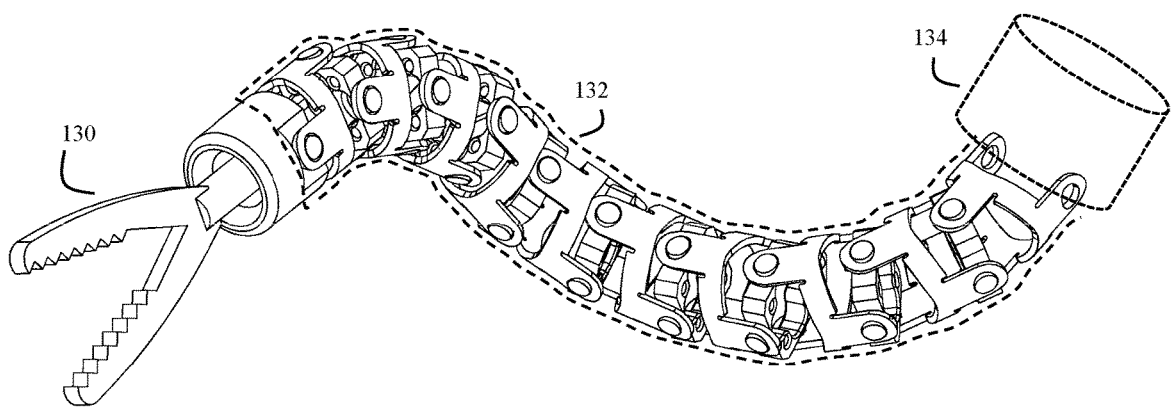
FIG. 2 shows a longer section of an articulated surgical device comprising multiple yoke and link units. Here the device also has an effector unit, here a grasping tool, attached to the most distal unit of the device. In some embodiments, the movement of at least the most distal unit is controlled by various pull wires (often four independently operated pull wires), that pass through small pull wire holes in the various units.

FIG. 2 shows a longer section of an articulated surgical device comprising multiple yoke and link units as per FIG. 1A. The device also has an effector unit (130), here a grasping tool, attached to the most distal unit of the device. In some embodiments, the movement of at least the most distal unit or yoke is controlled by various cables or pull wires (often four independently operated pull wires, see FIG. 4A-4C), that pass through holes in the various units, links, and yokes. These may often terminate at or near the most distal unit, link, or yoke. In embodiments where the surgical device is intended for use inside the body, the outside of the device is often covered with a flexible coating or layer (132), often made of a biocompatible polymer, to facilitate passage of the device though various body pathways. In some embodiments, the most distal link may sometimes be attached to the most distal yoke without any moveable link joints, so that cables or wires terminating in the most distal yoke can, by manipulating the angle of that yoke, more precisely control the orientation of the most distal link.

The proximal portion of the device (134) will often be connected to a larger control mechanism, such as a motorized control that allows the surgeon to guide the surgical device through various body pathways using a combination of force applied to the proximal units, as well as by manipulation of the various pull wires or cables passing through the device from distal to proximal that allow the distal portion of the surgical device to be manipulated through one or more axes as the device advances. This control mechanism (134) often remains outside of the patient's body.

The distance from the linkage to the control unit (134) will often be quite long, so intermediary sections of other materials, such as less flexible catheter material, can, in some embodiments, make up the extra length in between (132) and (134).

In a preferred embodiment, the articulated surgical device comprises hypermobile units comprising link and yoke units, as previously shown in FIG. 1A. However, although many of the examples herein show hypermobile units, other types of units, such as the units shown in FIG. 1B, may also be used.

FIG. 3A-J show a detailed close up of a link (106), yoke (104), link (a unit and a half) from FIG. 1A. As can be seen, the link (106) on the left is connected to the yoke (104) by one yoke pivot boss, producing a first axis of rotation (108). The link on the right is connected to the yoke (104) by a different yoke pivot boss, producing a second axis of rotation (110). This enables the hypermobile series of units to simultaneously swivel up and down, and from left to right as shown. In FIG. 3A-J, assume that all configurations are possible by suitably manipulating the various wires or cables (FIG. 4A 112, FIG. 4B 112) by a control unit (134).

Figure 4A:
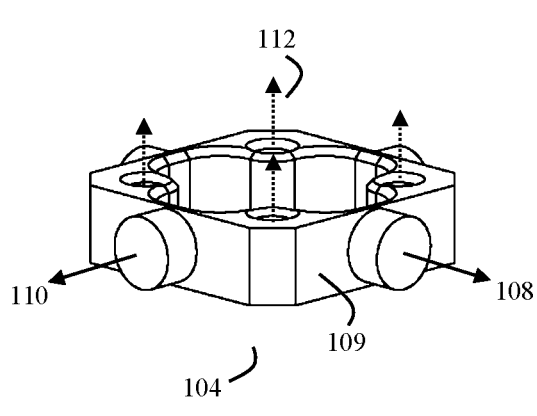
FIG. 4A shows a close up of the yoke portion of a hypermobile unit from a first angle, with the dotted arrows showing how the optional pull wires can pass through holes in the yoke.

FIG. 4A shows a close up of the yoke portion (104) of a hypermobile unit from a first angle, with the dotted arrows (112) showing how the optional pull wires or cables can pass through holes in the yoke. Note that there are four pull wires, and pressure on these different pull wires can cause the distal unit (or yoke) to rotate in either direction over the two different axis (108, 110).

Figure 4B:
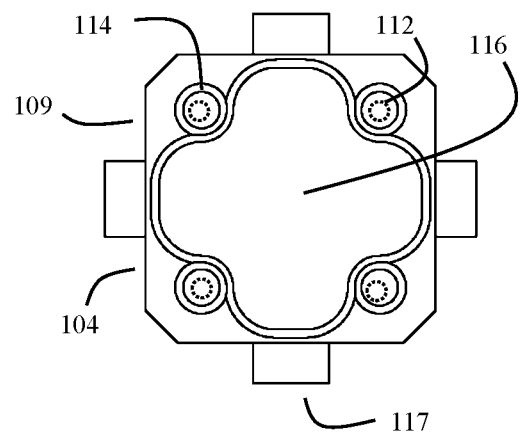
FIG. 4B shows a close up of the yoke portion of a hypermobile unit from a second angle, with the dotted circles showing the optional pull wires (cable feeds) passing through the yoke holes.

FIG. 4B shows a close up of the yoke portion (104) of a hypermobile unit from a second angle, with the solid circles (114) showing holes, and the dotted circles (112) showing how the optional pull wires (cable feeds) can pass through the yoke holes (114). The center of the yoke (116) is open to create an interior working channel through which various components can travel.

Figure 4C:
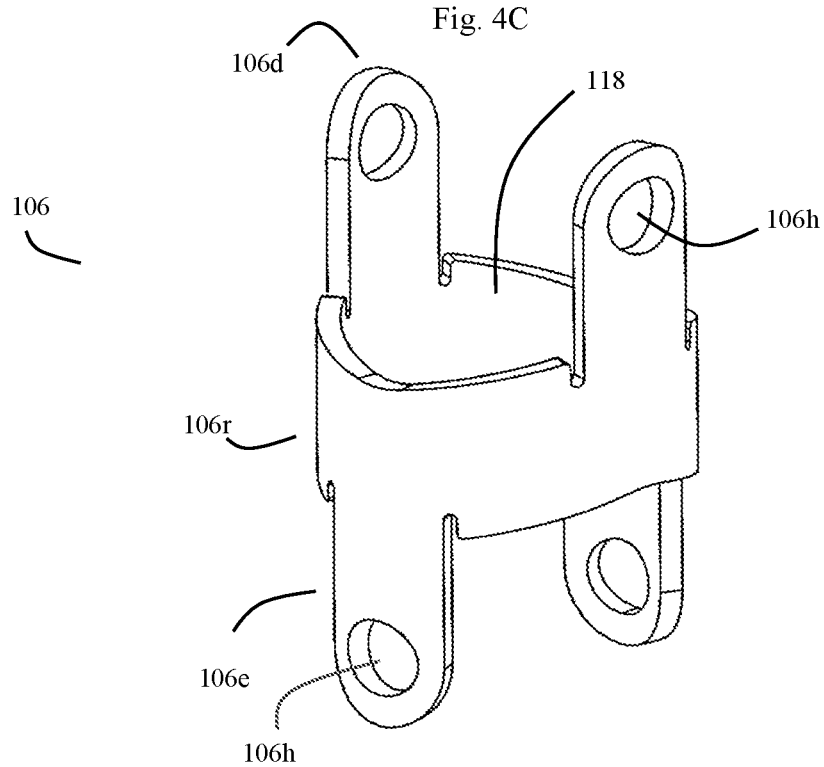
FIG. 4C shows a perspective view of the hypermobile unit's link portion.

FIG. 4C shows a close-up perspective view of the link portion (106) of a hypermobile unit. Here the optional pull wires or cables (shown above as 112) can pass through the center of the link (118). This is because the center of the link (118) is also open, again to create an interior "working channel" in conjunction with the corresponding yokes, since both are open in this region.

Figure 5:
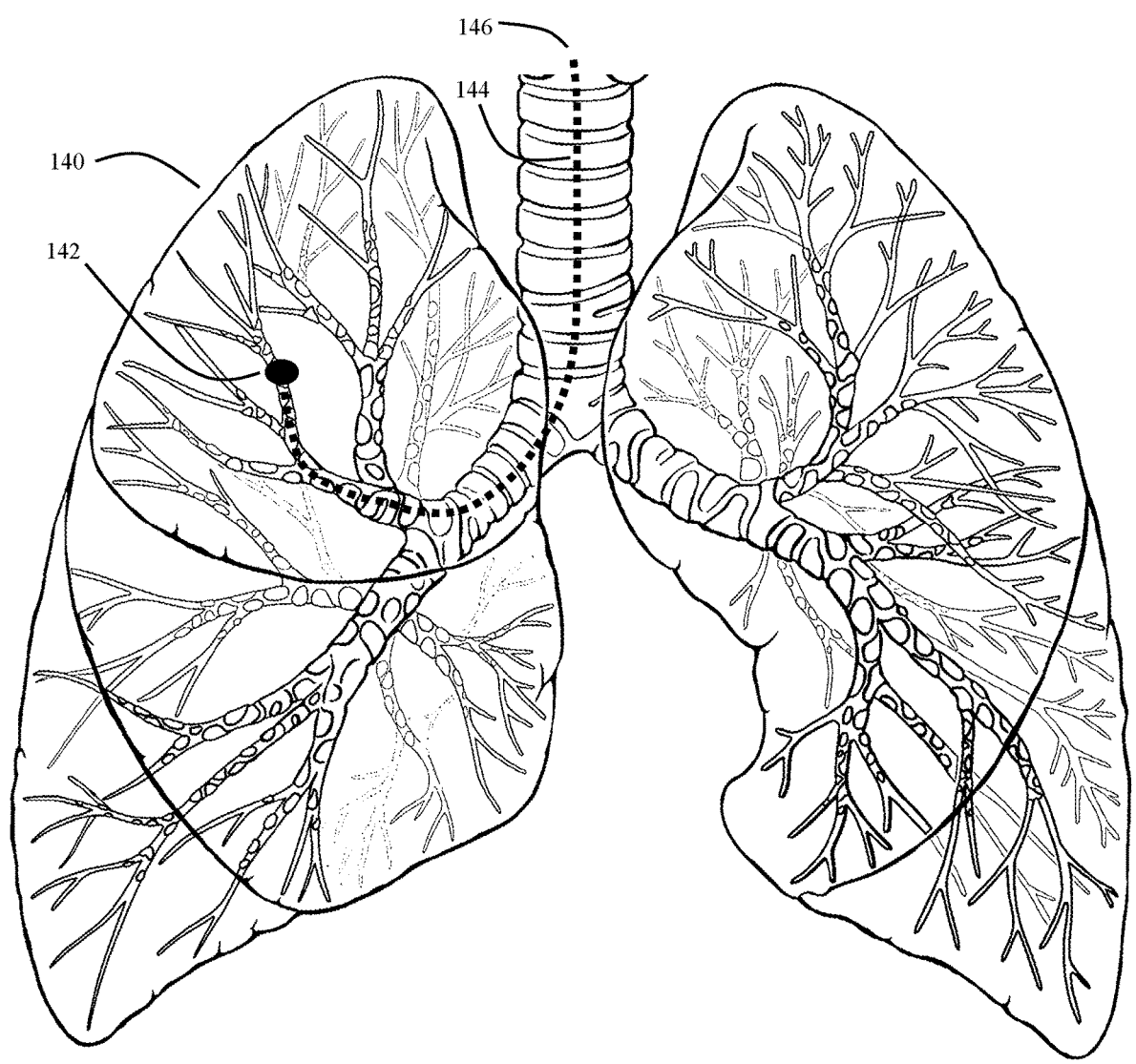
FIG. 5 shows an example of a surgical device pathway(s). Here, these pathways comprise at least some of the lumen of the patient's bronchial tubes and bronchiole of a patient's lung. Here, assume that the small dark circle on the left represents a target body lesion, located on the difficult-to-access outer third area of the lungs, that the patient's physician wishes to access with a custom manufactured articulated surgical device.

FIG. 5 shows an example of the surgical device pathway(s) discussed in this disclosure. In this example these pathways can comprise at least some of the lumen of the patient's bronchial tubes and bronchiole of a patient's lung (140). Here, assume that the small dark circle on the left represents a target body lesion (142) that the patient's physician wishes to access with a custom manufactured articulated surgical device, such as the device in FIG. 2. The dotted line (144) represents the pathway that the articulated surgical device may need to traverse to reach the target (142) from the entry point (146). As discussed, the present disclosure teaches automated methods to design and manufacture suitable surgical devices to accomplish this goal.

Note that FIG. 5 is credited to Patrick J. Lynch, medical illustrator, C. Carl Jaffe, MD, cardiologist, and is used under license by the Creative Commons Attribution 2.5 License 2006.

As previously discussed, in some embodiments, the invention may be a computerized system or method of manufacturing an articulated surgical device (see FIG. 1A 100, FIG. 1A, 120). Using methods terminology, the method may comprise receiving, into computer memory, surgical device pathway data (See FIG. 5, 144) describing at least some structural dimensions of a patient's body lumen or other internal body passage. Additionally, target location data (142) describing at least one target location in the patient's body, and its location relative to the surgical device pathway data is also received into the computer memory.

Additionally, other information, such as articulated surgical device design parameters, also needs to be present in computer memory. In some embodiments, this, articulated surgical device (sometimes called the articulated device, device, catheter, robotic catheter, or robotic device) comprises a plurality of connected units (102, 122). At least some of these units will typically have any of variable diameters and lengths.

Figure 1B:
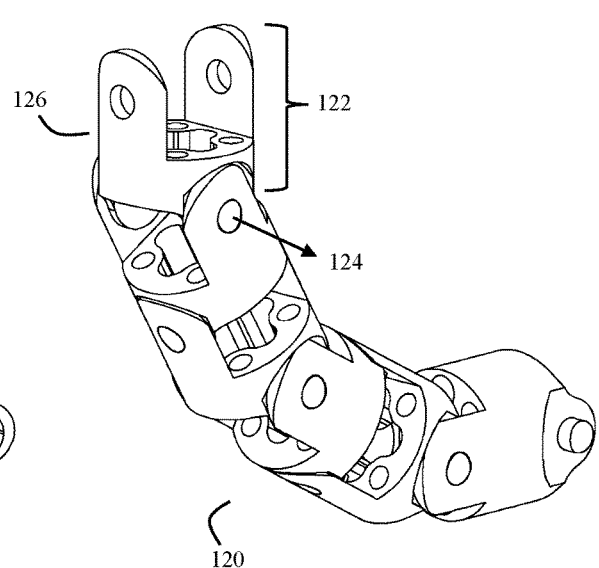
FIG. 1B shows an alternate example of an articulated surgical device, in this alternative embodiment, the device is also made up of repeating articulated units, where each unit comprises only one type of link, and each link is able to rotate about only one axis.
Figure 8:
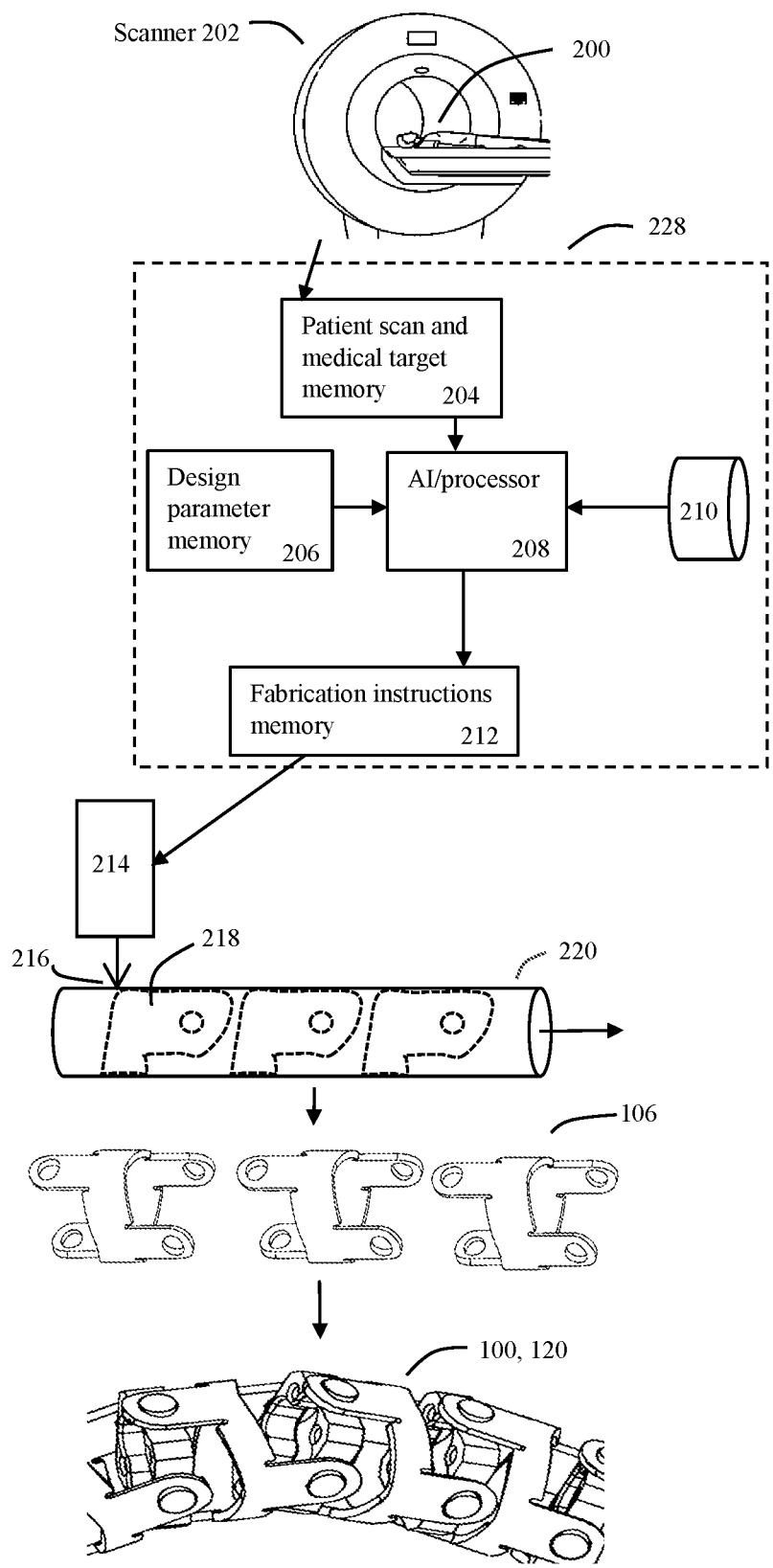
FIG. 8 shows an example of some of the equipment that may be used to automatically produce at least portions of the surgical device, such as entire units or at least portions of the units.
Figure 9:
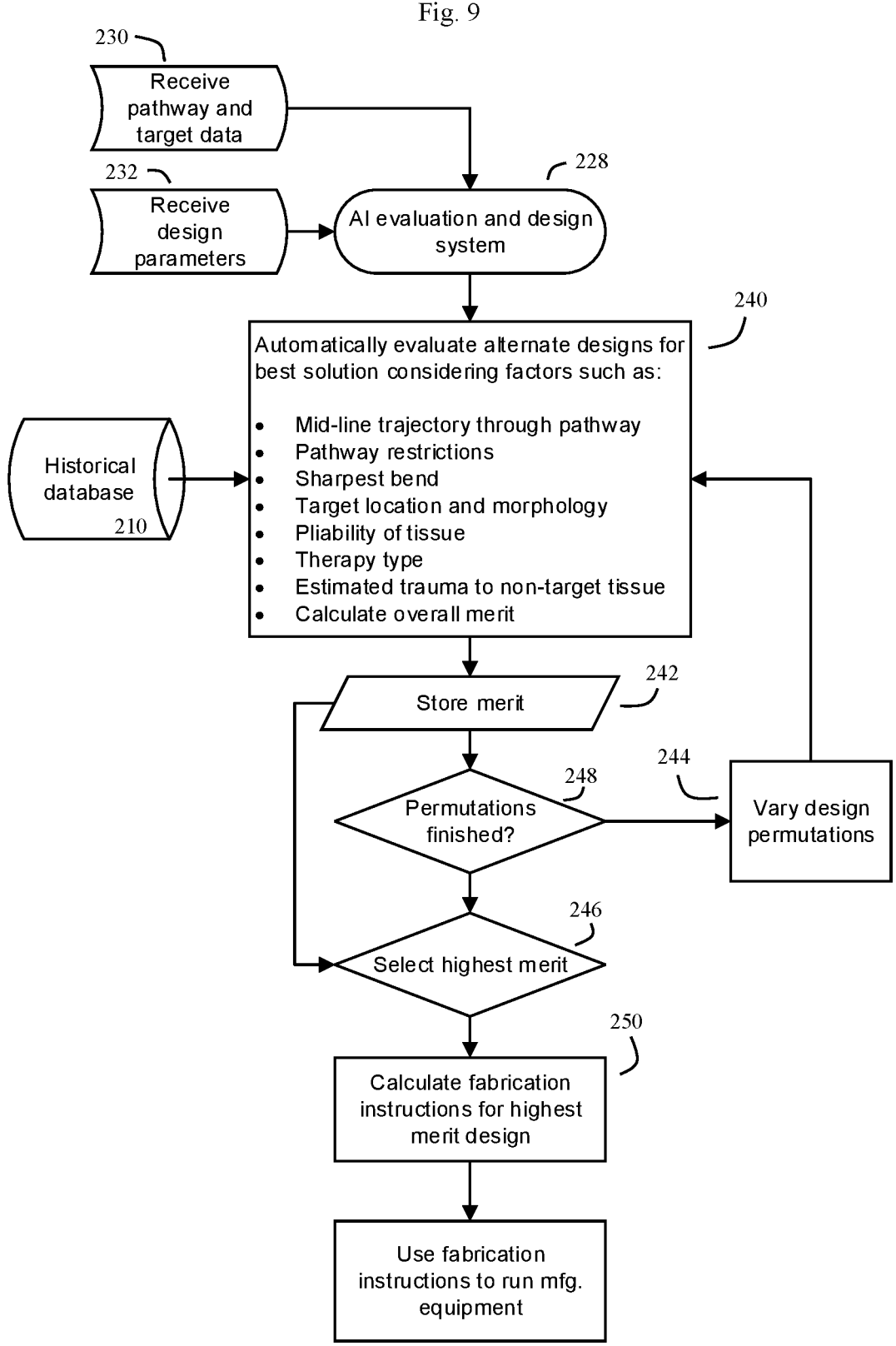
FIG. 9 shows a flow chart showing some aspects of the invention's computerized design and manufacturing methods.

More specifically, as shown in FIGS. 1A and 1B, these units further comprise at least one movable joint (108, 110), and configured to move about at least one axis (108, 110). As shown in FIG. 8 and FIG. 9, the method typically uses at least one computer processor (208), the surgical device pathway data (144), at least one the target location data (142), and the articulated surgical device design parameters to automatically design a patient customized articulated surgical device (such as FIG. 2 or FIG. 7). This device is configured to traverse a pathway (144) between an entry point (146) on the patient's body lumen or other internal body passage, along the patient's body lumen or other internal body passage (144), and to at least one target location (142). This design can then be used to automatically fabricate at least portions of this articulated device.

Figure 6:
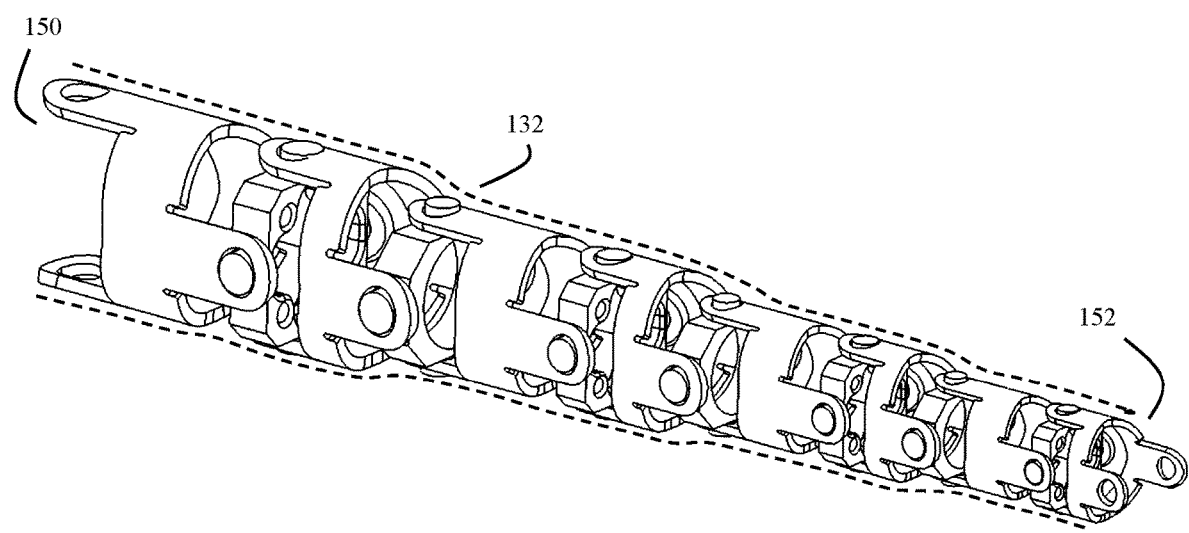
FIG. 6 shows an example of how a multiple unit articulated surgical device can be tapered from an initial wider proximal diameter to a narrower distal diameter.

FIG. 6 shows an example of how a multiple unit articulated surgical device can be tapered from an initial wider proximal diameter (150) to a narrower distal diameter (152). Here, although the units have the same general design, the initial proximal units are both wider and longer than the final distal units. As previously discussed, the dashed lines (132) show the approximate position of the polymeric sheath or covering that will often surround the device to minimize interactions between the sides of the device and patient tissues during insertion and removal.

Figure 7:
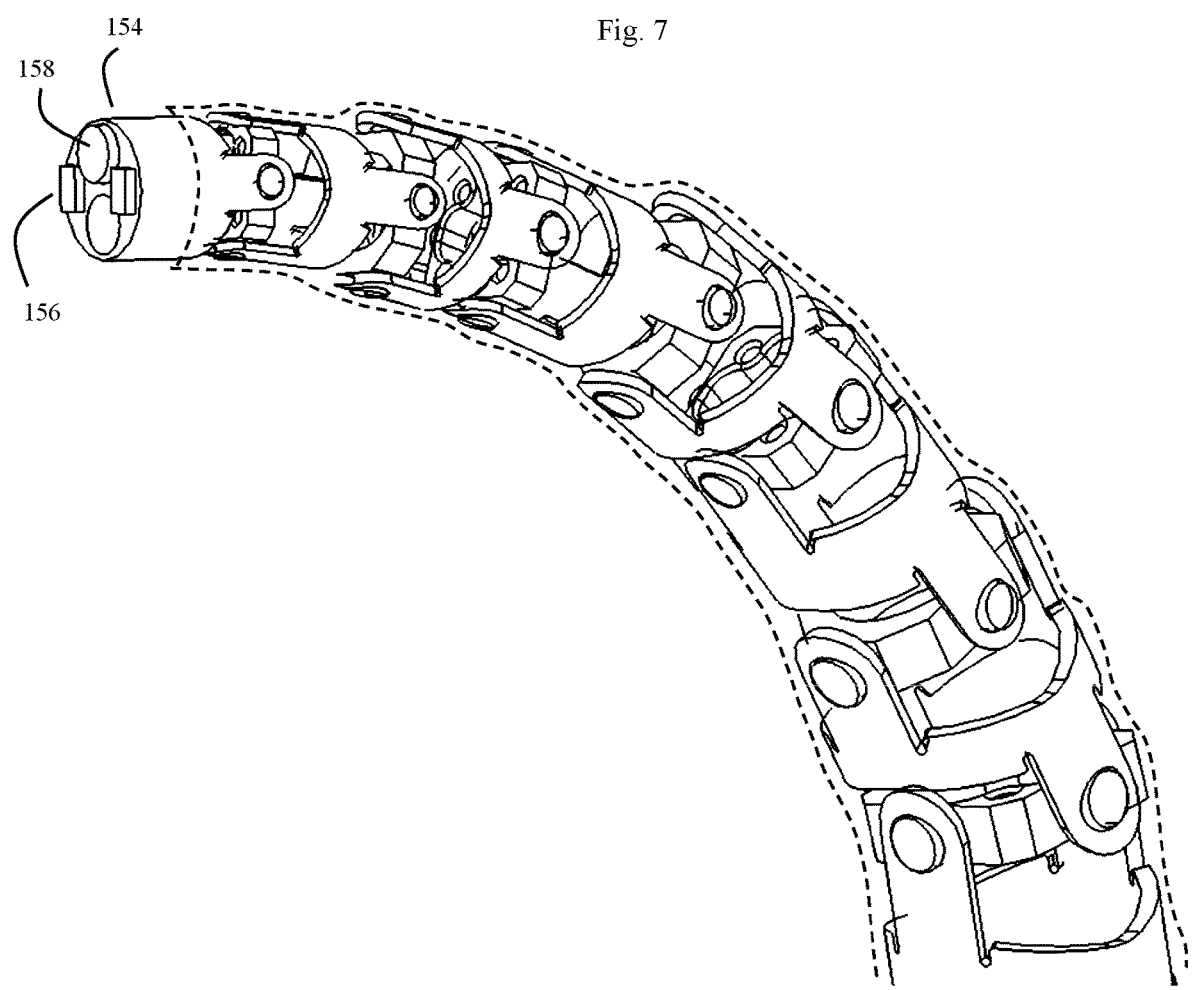
FIG. 7 shows an example of a tapered multiple-unit articulated surgical device, similar to FIG. 6, further equipped with a camera comprising both a light source and any of optical fibers or cameras and working channel at the distal end.

FIG. 7 shows an example of a tapered multiple-unit articulated surgical device, similar to FIG. 6, further equipped with a camera comprising both one or more light sources (such as LED light sources 156) and any of optical fibers or cameras (158) at the distal end (154). Here the working channel (formed the large empty regions 116 and 118 shown in FIGS. 4B and 4C) is generally hidden, but runs through the center of the device.

FIG. 8 shows an example of some of the equipment that may be used to automatically produce at least portions of the surgical device, such as entire units or at least portions of the units.

The method can be implemented according to various options.

In some embodiments, the surgical device may be customized for a particular patient. In other embodiments, a range of more standardized surgical devices may be created, each optimized for a different class of patients or class of surgical targets. If a given patient and surgical target can be adequately covered by an available standardized surgical device, then the standardized surgical device may be used. If not, then a customized surgical device may be created. Here, let us assume that the patient needs a customized surgical device.

For a customized surgical device, it will often be useful to acquire specific data pertaining to the structural dimensions of that patient's body lumen or other internal body passage intended for that surgical pathway. The location of the surgical target will also be needed. In this example, assume that this data is acquired by a suitable medical imaging scan, such as a CAT or CT scan, MRI scan, ultrasonic scan, X-ray, or other modality (202).

As shown in FIG. 8, to do this, the patient (200) may be scanned by medical scanner (202). The resulting medical scan data (which may be annotated to point out the desired surgical pathway and target) is transferred into computer memory (204). Additional data, such as the design parameters for the desired surgical device may also be transferred (if it is not previously present) into computer memory (206). This information is then processed by at least one computer processor (208). This at least one computer processor can be chosen from the ARM, x86, MIPS or other processor families, and in some embodiments may be further comprise additional AI (artificial intelligence) hardware such as specialized neural net or AI processors (NPU), Graphics processors (GPU), FPGA (field programmable gate arrays), and co-processors. Examples of suitable NPU and GPU processors include the Intel NCS2 chip, Telum processor, Nvidia DGZ A100, Google Cloud TPU, Edge TPU, Cerebras WSE-2, and others.

The AI/processor system (208) will take the patent scan and medical target data, the design parameters relative to the type of articulated surgical device desired, and (often supplemented, or trained by a historical database of other articulated surgical devices/pathway—target situations) and determine an articulated surgical device that best satisfies the various constraints. See FIG. 9 for more detail.

Once the overall design is determined, either AI/processor (208) or a different AI or processor unit can then determine the fabrication instructions (212) needed to create the various components of the articulated surgical device. These components can include the diameters and lengths of at least some of the various units or portions of the units (102, 104, 106, 122, 126), and other components as desired. (As previously discussed, in some embodiments, unit 122 can consist of link 126.)

These fabrication instructions (212) can also be stored in computer memory (212). In some embodiments, certain portions of at least the memory (204, 206, optionally historical database 210), the AI/processor 208 and/or fabrication instruction memory (212) may be packed as a single unit (228), often referred to here as the AI system, but such packaging is optional.

Certain portions of the articulated standardized device, in particular the control unit (134), and possibly the effector units (130) (i.e., the "payload" at the distal end of the catheter, often configured to perform a medically useful task), may often be standardized and pre-fabricated units. However often the middle portion of the device (e.g., at least some of the various units) may be customized to that particular patient/pathway/target situation.

In some embodiments, the fabrication instructions (212) may be used to operate various types of automated manufacturing equipment, such as CNC (computer numerical control) machining devices, computerized laser cutting devices, and the like. In FIG. 8, these instructions (212) are shown operating a laser cutter (214), which is cutting (216) various subunits of various dimensions, such as precursors (218) to the units or subunits (106, 122, 126), from a stock material such as a hollow hypodermic tube (218). This tube can made from stainless steel or other surgical grade material.

After optional further processing, these precursors (218) become surgical device units or subunits (e.g., 106, 122, 126), which can then be further assembled to form longer portions of the articulated surgical device (100, 120). After assembly, these form a completed articulated surgical device (FIG. 2, FIG. 6, FIG. 7) customized to that particular surgical pathway and target situation.

FIG. 9 shows a flow chart showing some aspects of the invention's computerized articulated surgical device design and manufacturing methods.

As previously discussed, the process will often begin by receiving pathway and target data into computer memory (204), (230). This will typically include surgical device pathway data describing at least some structural dimensions of a patient's body lumen or other internal body passage. Additionally, the process often requires entering additional information into computer memory, such as target location data describing at least one target location (142) in the patient's body, and its location relative to the surgical device pathway data (144).

The method also requires computer memory configured with the articulated surgical device design parameters (232), as previously discussed. For example, this articulated surgical device will usually comprise a plurality of connected units (102, 122). Often, at least some of these units will have any of variable diameters and lengths (see FIG. 6 and FIG. 7).

As previously discussed, this plurality of units (102, 122) will usually further comprise at least one movable joint (108, 110, 124), configured to move about at least one axis (108, 110, 124).

The method then uses at least one computer processor (e.g., AI/processor 208), the surgical device pathway data (144), at least one target location data (142), and said articulated surgical device design parameters to automatically design a patient customized articulated surgical device configured to traverse a pathway between an entry point (146) on the patient's body lumen or other internal body passage, along said patient's body lumen (144) or other internal body passage, and to this at least one target location (142).

Some factors that the automated system (228) or method may consider include evaluating (either iteratively, or through AI methods), a plurality of alternate candidate articulated surgical device designs.

In some embodiments, for at least some of these designs, the system/method can calculate a plurality of different paths that a given candidate articulated surgical device may traverse along said pathway (144) between an entry point (146) and said target (142). Here, keep in mind that a different surgical device made with different sized units will often traverse somewhat different paths.

For at least some of the various candidate articulated surgical devices, the at least one computer processor (208) can evaluate the diameters of the given candidate articulated surgical device along the pathway (144). The processor can also evaluate the ability of at least some of the units of a given candidate articulated surgical device to bend along a given pathway. The processor can also evaluate the ability of at least some proximal units (150) of said given candidate articulated surgical device to drive and/or guide distal units (152) of said given candidate articulated surgical device as said distal units approach said target (142).

These considerations are discussed in more detail in FIGS. 10-15.

According to the method, the at least one computer processor (208) can preferentially select those designs that meet preset criteria. These preset criteria can comprise various factors, such as minimizing calculated trauma to any sides of said pathway (144) between the entry point (146) and the target (142).

Such criteria need not be complex. For example, a simple Hook's law or other mechanical stress and strain type calculation, where the force exerted by the surgical device spring action against body tissue, can be used. Here, the greater, the force, the greater the calculated trauma, where the coefficient of damage can be generated experimentally. Other types of polynomials or functions may also be used. In any event, the amount of pressure exerted by the device against non-target tissue should generally be minimized.

Figure 10:
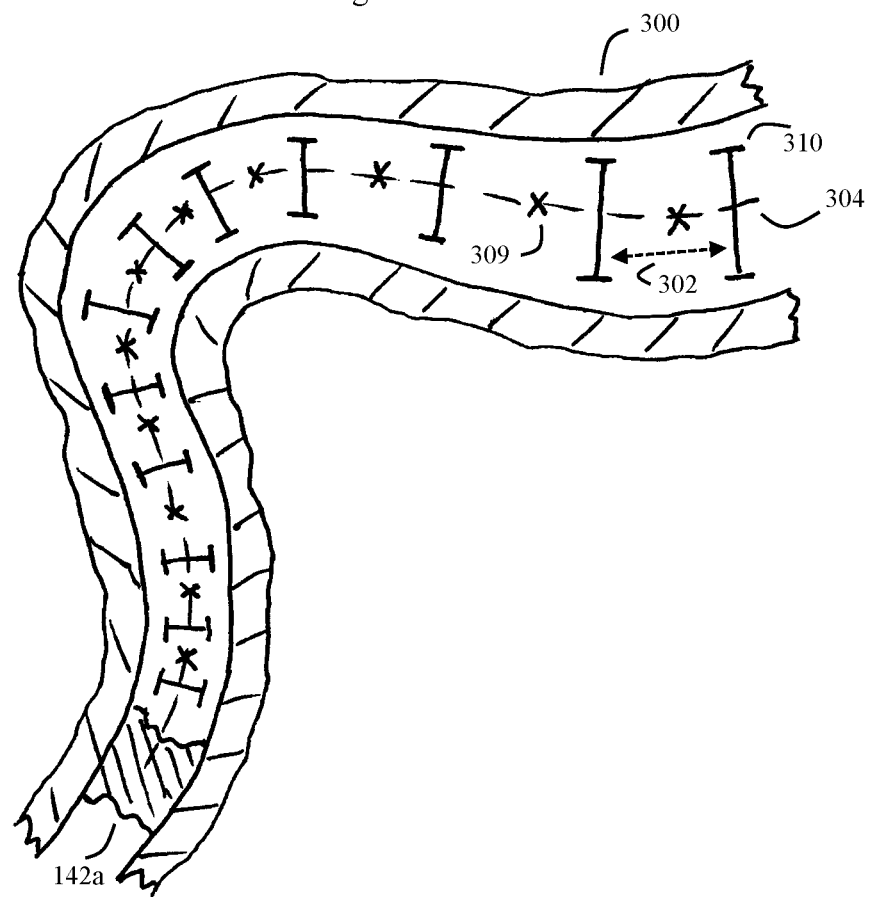
FIG. 10 shows an example of some factors considered by the invention's automated design system. As the device traverses the body pathway, the diameters of the various units (brackets 310) should generally narrow as the width of the pathway shrinks. The joints or turning radius between the various units is also shown.

FIG. 10 shows an example of some of the factors that may be considered by the invention's automated design system (228). As the device traverses the body pathway (144), the diameters of the various units (310) may be configured to generally narrow as the width of the pathway shrinks (see FIG. 5). The position of the joints between the various units is also shown. The software can be given general guidelines, such as that a larger diameter is preferred when openings are large, a smaller diameter is required to enter narrower pathways, and the device must be configured to reach a given target.

In this diagram, the body vessel or lumen walls are shown as (300). The distance between the units is shown as (302). The centerline of the surgical device's proposed pathway is shown as (304). Here the target (142*a*) is a concentric lesion with a concentric morphology that is totally blocking the vessel.

As a simplified example, the AI system can generate a trajectory path, and create unit diameter fiducials as well as calculate an optimal distance between units. Here the AI system is generating an initial "stick" map that can then convert to the lengths of the units, as well as the type of yokes (if any) used in these portions of the device.

For some designs where the units comprise both yokes and links, after the diameters of the units are calculated, the software can then optimize the positions (e.g., length of the links, or at least the length of the link arms) and determine where the yoke and their corresponding yoke pivot points should be located.

In some embodiments, after the trajectory path with diameter fiducials are mapped, the system can then locate the positions for the ideal yoke pivot locations (312).

Figure 11:
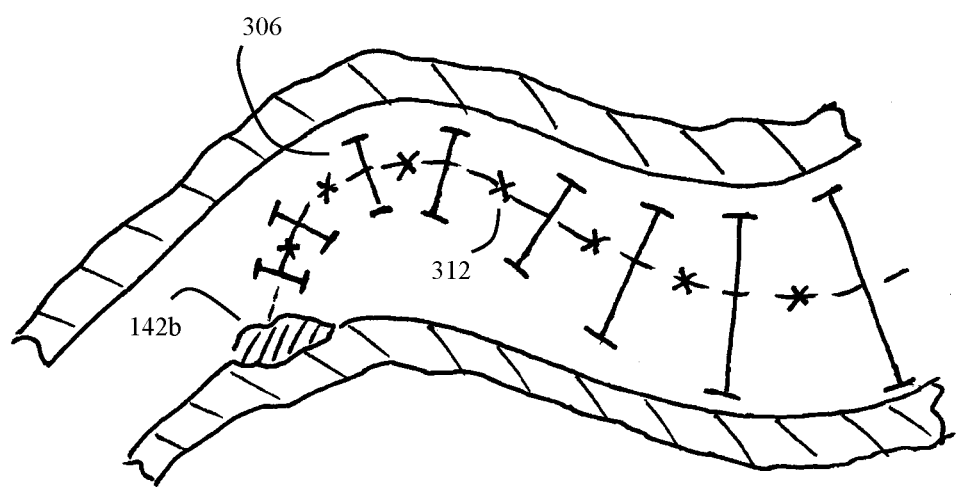
FIG. 11 shows that the automated design software can also be given additional design guidelines. Here a sharp angle of attack (sharp bend) is needed to effectively treat a given target, which is located on the side of the body lumen.

FIG. 11 shows that the automated design software can also be given additional design guidelines. Here the target (142*b*) is an eccentric lesion located on the vessel walls. As a result, a sharp angle of attack (sharp bend 306) is needed to effectively treat this target, which is located on the side of the body lumen. Here the software can, for example, reference historical data of previous successful designs for further design constraints.

Specifically, for a sharp angle of attack, the AI system can be trained using historical data (210) for successful designs that had previously worked adequately with this type of situation. This historical data can also include additional factors, such as loads on any robotic motors (134) used to drive the unit, and the location of the target (lesion). Note that in FIG. 11, the distal section transitions from a small diameter, capable of a tight bend radius, to a larger proximal diameter used to stabilize the device and support the distal loads while force and work is being transmitted to the target lesion (142*b*).

Figure 12:
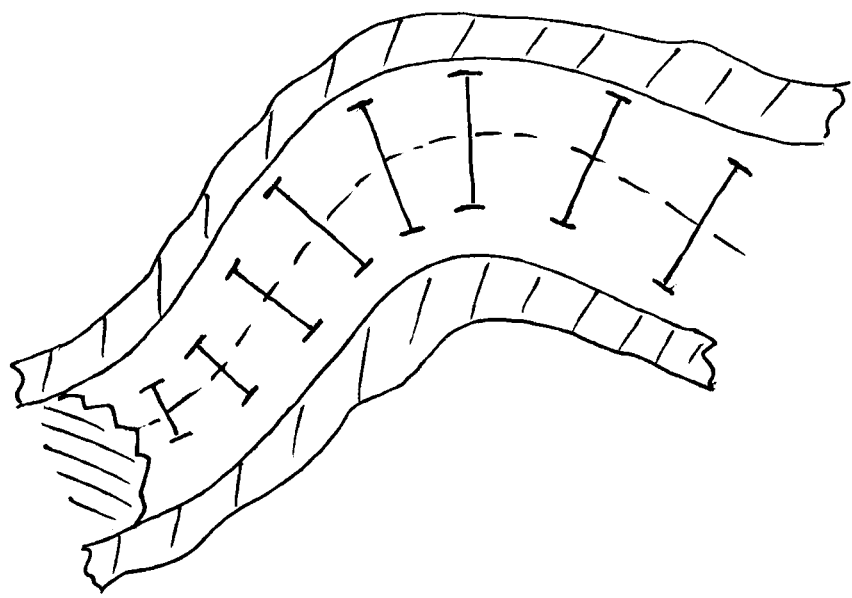
FIG. 12 shows how in some embodiments, the automated design software can follow a design guideline to configure the diameter of the units to match the size of the body lumen.

FIG. 12 shows how in some embodiments, the automated design software can follow a design guideline to configure the diameter of the units to match the size of the body lumen. Here the AI system can generate diameter fiducials (diameters of the units) that match closely to the vessel/lumen's change in diameter, as well as the type of distal tip (effector unit) necessary for examining or treating a particular target. In this example, the distal portion of the surgical device is made smaller for the type of work required. While moving proximally, the diameter steps up. In this case, the device as a whole is made to follow the natural tape of this body vessel/lumen.

Figure 13:
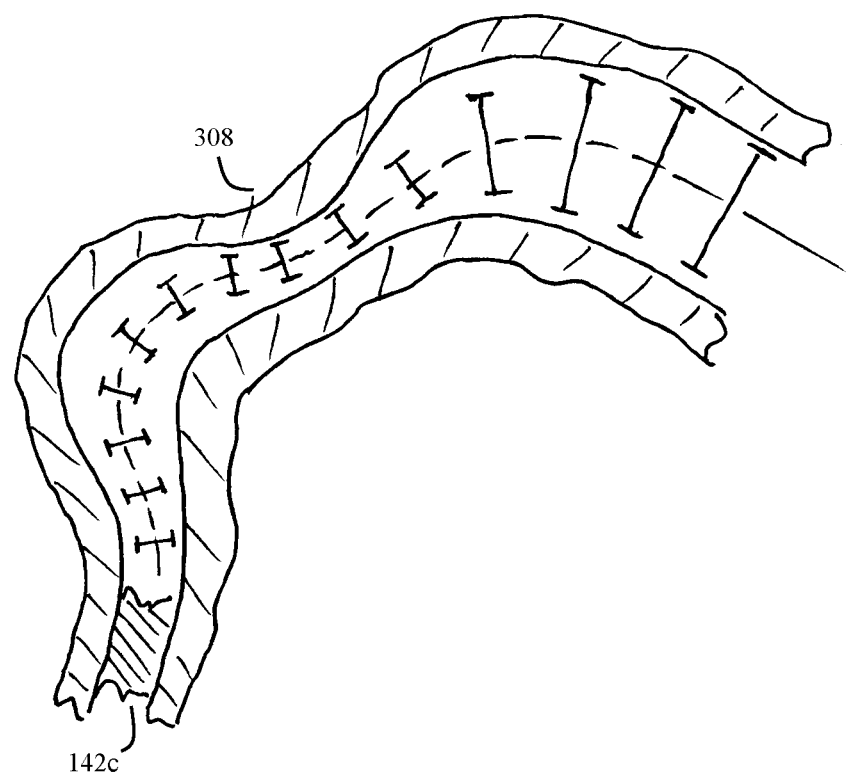
FIG. 13 shows that in some restricted path situations, the automated design software can follow a design guideline to create a "neck" with wider regions before and after a restriction, but with a narrowed region at the restriction.

FIG. 13 shows that in some restricted path situations, the automated design software can follow a design guideline to create a "neck" with wider regions before and after a restriction (308), but with a narrowed region at the restriction. Here the computer system can calculate if, given that design, the device can use force, transmitted by the wider units proximal to the neck, help ease the device through the restriction.

Specifically, for a restricted path, the AI system can generate a necked down section to get beyond the restriction (308), and to the target lesion location (142*c*). To apply stability to the device, the proximal section transitions rapidly to larger diameters. The AI system can also be configured to use historical data from robotic motor loads (134) to create the appropriate step-up in transition from distal to proximal in the hyper flexible steering portions of the device.

Figure 14:
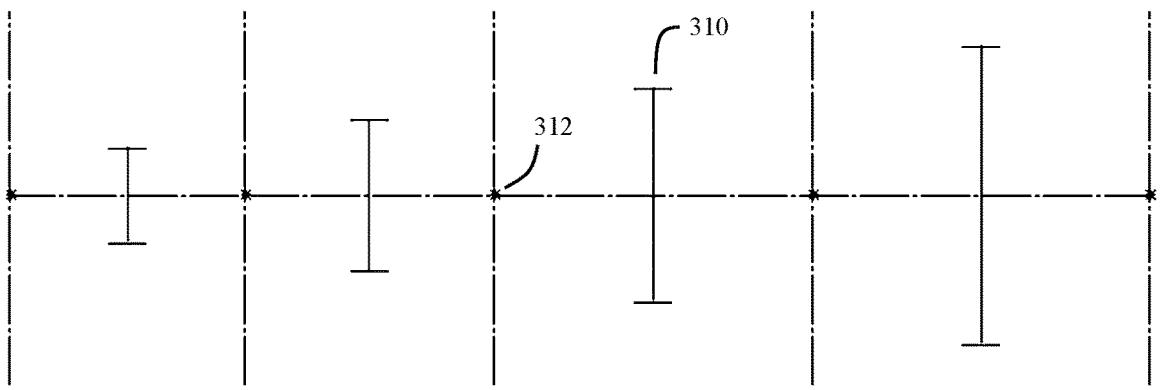
FIG. 14 shows an abstracted version of some of the automated design software design guidelines. Here the brackets show a given set of unit diameter parameters, and the intersecting stars show a given set of pivot point parameters (which can be controlled by the lengths of the units, and/or yoke locations).

FIG. 14 shows an abstracted version of some of the automated design software design guidelines. Here the brackets show a given set of unit diameter parameters (310), and the intersecting stars (312) show a given set of pivot point parameters (which can be controlled by the lengths of the units, and/or yoke locations). In some embodiments, the automated design software can either iterate over a range of such parameters, and/or use AI methods, such as neural net techniques, to again effectively consider a range of alternative designs, and pick those with the best merit according to a merit algorithm.

Figure 15:
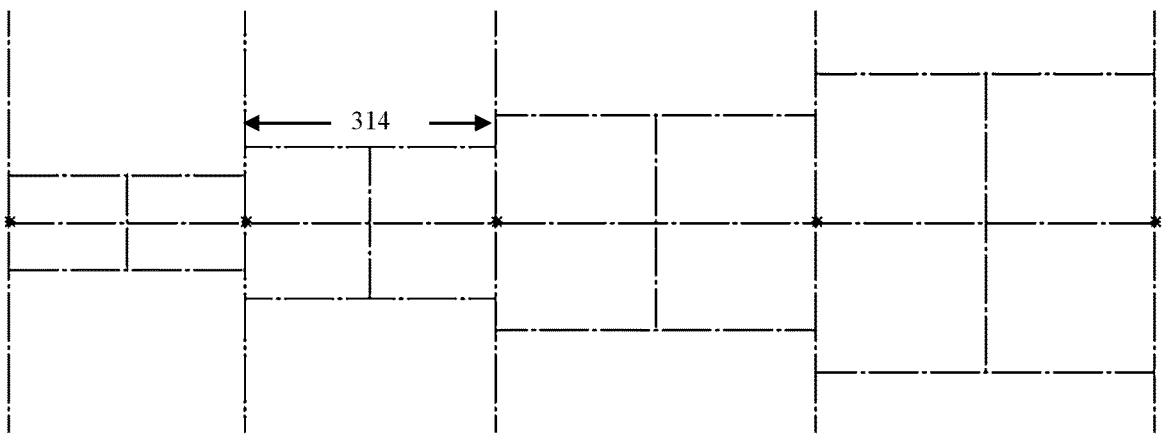
FIG. 15 shows a later stage in the automated software design process. Here, after a preferred set of unit diameters and pivot points has been chosen, the automated design software can then use these parameters to then compute other aspects of the design, such as the design of the individual yokes and links.

FIG. 15 shows a later stage in the automated software design process. Here, after a preferred set of unit diameters (310) and pivot points (312) has been chosen, the automated design software can then use these parameters to then compute other aspects of the design, such as the lengths of the individual links. This information can then be sent to suitable manufacturing equipment, such as CNC laser cutters, CNC machine devices, or 3D printing devices (214). Here the lengths of the links (106), (126) are shown as lines (314).

As will be discussed in more detail shortly, in some embodiments, the computerized system can evaluate the ability of at least some proximal units (150) of a given candidate articulated surgical device to drive and/or guide distal units (152) of said given candidate articulated surgical device as said distal units approach said target (142) using criteria such as:

a) The distance from said target (142) to any proximal end motorized drive control head (134).
b) The output of any motor (134) used to drive a proximal end of said candidate articulate surgical device.
c) The estimated mid-line trajectory (304) of a candidate articulated surgical device as it transits a distance along said pathway from said entry point (146) to said target (142).
d) The estimated sharpest bend (308) of a candidate articulated surgical device as it transits a distance along said pathway from said entry point (146) to said target (142).

e) A smallest lumen or vessel diameter along a trajectory along said pathway between said entry point 146 a said target location (142).

f) The dimensions and characteristics of body lesions or abnormalities present at said target location (e.g., 142a, 142b, 142c).

g) The restrictions (308) along said pathway between said entry point to said target with a potential of impeding passage of a candidate articulate surgical device.

h) The estimated pliability of any sides (300) of said pathway between said entry point (146) and the target (142).

i) Type of therapy projected to be applied at said target. This is often determined by the choice of effector unit placed at the distal end of the device.

As shown in FIG. 8, this method (and system 228) can then use this design (and fabrication instructions, often stored in memory 212) to automatically fabricate (214, 216, 218, 220, 106) at least portions (100, 120) of the articulated device.

As previously discussed, according to this method, the surgical pathway data (144) comprises (or is obtained from) at least one 3D image obtained from imaging scans (202) of the patient (200). Further, the target location data comprises a location (142) in the patient's body that can be accessed by traversing the patient's body lumen (144) or other internal body passage.

As previously discussed, in a preferred embodiment, the at least one processor (208) implements these various automatic considerations by any of artificial intelligence type machine learning or a predetermined computer algorithm.

FIG. 9 also shows how, in some embodiments, the processor can alternatively implement these considerations (240) as an iterative process. Here, the processor can consider one design based on a first set of design parameters (first permutation). The processor can then assign and store a merit to this first design (242), by weighting the various factors. For example, the design can be assigned a higher merit for every design rule followed, and a lower merit for every design rule not followed, and the results evaluated according to a weighting function where each rule can be assigned a different weighting value as needed. The system can then iterate (244) through a series of design permutations, and select the highest merit (246) at the end (248). An AI type method may alternatively use historical database trained neural networks (210) to achieve the same end. The system can then calculate the fabrication instructions (212, 250), for the highest merit design.

FIG. 9 also shows an example of how the automatic fabrication instructions can be used to operate automatic production equipment to produce at least portions of the surgical device, such as entire units or at least portions of the units.

As previously discussed, in some embodiments, the automatic fabrication method comprises generating instructions to operate any of a CNC machining, CNC laser cutting device, or 3D printing device (214).

More specifically, in some embodiments, this automatic fabrication further comprises using said instructions to operate any of a CNC machining, CNC laser cutting, or 3D printing device, thereby producing unit portions comprising at least portions of said units (such as 218, 106). These unit portions can then be assembled into at least portions of the articulated surgical device (100, 120).

In some embodiments, this CNC machining or CNC laser cutting or 3D printing device further uses at least one hypodermic tube (220) as a starting material to produce these unit portions. For CNC machining, a solid bar stock of metal may also be used.

As previously shown in FIGS. 6, and 7, as well as FIGS. 10-15, in some embodiments, the design further comprises units of varying lengths and diameters, such that the diameters of the units on a proximal side (150) of said articulated surgical device are greater than the diameters of said units on a distal side (152) of said articulated surgical device; and said lengths of said units on a proximal side (150) of said articulated surgical device are greater than the lengths of said units on a distal side (152) of said articulated surgical device.

As previously discussed, in some embodiments, according to the method, at least portions of said articulated device may further be covered with a flexible covering (132). In a preferred embodiment, this covering comprises a biocompatible polymer, often selected for minimal thrombogenic properties, flexibility, and ability to survive a sterilization process. Examples of suitable polymers include polyurethanes, polycarbonates, polyamides, fluoropolymers, polyolefins, polyimides, and the like.

This flexible covering is usually selected to reduce interaction between said articulated device and any of patient body fluids and/or non-target sides of the body lumen or other internal body passage. Additionally, the interior of said articulated device is configured with a working channel (FIG. 4B, 115) with dimensions often selected to enable at least some tools to traverse said working channel. In some embodiments, this can be from an entry point (156) to a most distal unit (152) of said articulated device.

As previously discussed, in some embodiments, at least some of said units are hypermobile units that further comprise at least two movable joints, and are configured to move about at least two axes (108, 110).

As shown in FIGS. 4A and 4C, these hypermobile units can further comprise a hypermobile link and a hypermobile joint, and at least some of said hypermobile joints further comprise a yoke (104) comprising a polygonal or circumferential base (109), forming a central opening (116) and having four vertically oriented pull wire holes (114) disposed at ninety-degree intervals from one another. The yoke further comprises four cylindrical pivot bosses (117) extending laterally from said base at ninety-degree intervals. This yoke is configured to couple with a first link (106a) from its unit (102), and a second link (106b) from a neighboring unit. The first link (106, 106a) is movably coupled with a first set of two of the four cylindrical pivot bosses and extending from the yoke in a first direction, such that the first link pivots in a first plane (108) relative to the yoke. The second link (106b) is movably coupled with a second set of two of the four cylindrical pivot bosses, thus extending from the yoke in a second direction, such that the second link (106b) pivots in a second plane orthogonal to the first plane.

As shown in FIG. 4C, in some embodiments, the first link (106a) comprises a first ring (106r), with a first set of arms (106d) extending vertically from the first ring in a first direction; and a second set of arms extending (106e) vertically from the first ring in a second, opposite direction. Referring to FIGS. 3A and 4C, in some embodiments, the second link (106b, which is otherwise identical to the first link) comprises a second ring and a third set of arms (106d) extending vertically from said second ring (not numbered) in a first direction. There is also a fourth set of arms (106e) extending vertically from the second ring in a second, opposite direction. Here as well, each arm of the sets of arms comprises a circular hole (106h) sized to fit over one of the four cylindrical pivot bosses (117) of the yoke (104).

As shown in FIGS. 4A and 4C, in some embodiments, the bases (109) of at least some of the yokes further comprise four vertically oriented pull wire holes (114) disposed at ninety-degree intervals from one another. Here a plurality of the articulated surgical device yoke bases further comprises four pull wires (112) disposed individually in each of said four pull wire holes (114).

As previously discussed, (see FIG. 6, FIG. 7, and FIGS. 10-15, in some embodiments, the articulated surgical device design further comprises links and yokes of varying lengths and diameters. Typically, the diameters of the links and yokes on a proximal side (150) of the articulated surgical device are greater than the diameters of said links and yokes on a distal side (152) of said articulated surgical device. Further, often the lengths of any of said set of arms (106d or 106e) on a proximal side of said articulated surgical device are greater than the lengths of said set of arms on a distal side of said articulated surgical device.

Further, as previously discussed, often at least one effector unit (130, 154), comprising any of a camera, grasping tool, cutting tool, monopolar or bipolar electrodes, tissue sampling device, radioactive seed, or radiation or drug administration device is attached to a most distal unit of said articulated surgical device.

Further Discussion

When combined with state-of-the-art imaging technology, pre-CT/MRI, a 3D model of the patient's access pathway to the target location can be generated. The 3D model provides significant information that is at present not being fully utilized for surgical devices. In a target centric approach, the design of a fully custom robotic catheter can become a reality.

With a robotic or articulated catheter system, stability, control, and precision can now be fully implemented in harder to reach areas through a customizable link-yoke catheter. These attributes can be leveraged by the motors (134) tensioning the steering cables (112) through the articulated surgical device to actuate and drive a tailored-to-patient 4-way steerable catheter.

The features of this articulated surgical device can be very small where they need to be (down to 1 mm diameter and 25-micron thick link wall for example). This allows a surgeon to perform the critical tasks by having the distal portion of the catheter locked in place at a precisely determined location based on pre-CT/MRI image/modeling and real-time CT/MRI imaging during the procedure. The latter eliminates CT-to-body divergence due to real-time imaging overlapping with the pre-determined path and target information.

One feature that helps creates stability in the catheter is how it transitions from a smaller diameter (OD) at the distal end (152) to a larger diameter (150) proximally. Ideally, the catheter becomes larger in diameter proximally with less mobility. The mobility portion is more concentrated close to the target distally. This allows for more stability in the catheter as it is controlled outside of the patient. The patient's anatomy both in the healthy entry portions of the vessel through which the catheter is driven, and the unhealthy or restrictive target portions, drive the design of the catheter over its length. Any patient anatomic anomalies also drive the design from the target. In a preferred embodiment, due to the scalability of the link-yoke catheter configuration, the 4-way steerable portion can be size reduced in a stepped fashion, thus providing for the more stability where it is required upstream. This feature can be useful to achieving high precision motion control at the target (142).

Although the present invention also operates with simpler designs, (see FIG. 1B), more complex designs, such as FIG. 1A, are often preferred. This link-yoke catheter provides the highest level of 4-way control in the smallest diameter with the largest inside diameter (or working channel). As a result, the catheter can be driven to the target (142) through a torturous path (144) with the ability to deliver vision, tools, and the necessary therapy. As seen in FIG. 5, this torturous path can have narrowing sections and abrupt turns. This is also key to the final precision at the target as it enables the delivery of the therapy to be properly articulated at, near, or over the target, depending on the biopsy or therapy type.

The precision of the link-yoke catheter in a biometrically custom design is enabled by two major technology advancements: 1) The ability to custom design the catheter to the patient's anatomy through a pre CT or MRI generated 3D image along with historical-learned data coming from an AI based system, and 2) The ability to create a 4-way steerable catheter with stepped diameters and variable length link sections that can be totally designed and built most cost effectively solely with computer automation using the most efficient processes.

Surgical precision, such as the ability to make small controlled motions in any direction, is often the final determining performance metric once the catheter's forward distal section is driven to the target. Having a catheter designed by AI based for the patient's unique anatomy and the learned information from previous patients can help provide a significantly greater benefit to the new patient.

To reiterate some earlier points:

The links and yokes are customizable or scalable in both diameter and length. This allows the length of the link or the diameter to vary individually (a tapered device). The ability to produce a progressively smaller distal portion enables a catheter to be engineered for a specific anatomy. The tapering can be important when moving from a vessel and branching to a smaller one. The descending diameter of the links create a perfect loading condition on the steering cables, where the far distal end bends in a smaller radius than proximally because there is more interleaving or space for the leading link to tuck deeper into the following link. Also, for a fixed or varying diameter, the longer links would be proximal and as the catheter length progresses distally, the links get shorter. This progressive increase in length and diameter proximally provides for more stability, control, and precision in a robotic catheter.

The scalability between a yoke and its corresponding links is also important. The yoke acts as a transition link (like a railway coupler), providing for a universally scalable steerable catheter. It is through the yoke that scalability can take place.

To summarize:

The link length and diameter are scalable. Further, the link length can vary, allowing for more links distally to create a tighter bend radius towards the distal tip. This can also be used to create a tapered articulated surgical device.

The yoke can act as a transition coupler between one diameter link to another link of different diameter enabling scalability of diameters.

Moving from a small distal diameter with short links to a larger diameter and length of the proximal links creates more stability, control, and precision in this articulated surgical device.

From a manufacturing perspective, the scalability is nearly free due to the catheter length coming entirely from the laser cut or 3D printed link. The links contribute all the length to the catheter. Because the links can be cut from hypo-tube with an automated laser, there is almost no tooling cost for adjusting the length. Likewise, the diameter of the hypo-tube is very easily changed by swapping out a collet and replacing the hypo-tube. Since there is no change in tooling, only the flat patterns in CAD are updated in software for length or diameter changes and these steps are fully automated.

As previously discussed, FIG. 6 shows a link-yoke catheter section with varying length and diameter links and both non-transition and transition yokes.

Also as previously discussed, FIG. 7 shows the tapered link-yoke system articulated to a certain bend radius with camera, LED lighting and working channel as would be used in endoscopic applications. In this case, the device has at least one camera (158), working channel for delivering tools (FIG. 4, 116, 118), and two LED lights (156). Coming off the tool plate (not shown) are four pull wires (see FIG. 4A and FIG. 4B, 112) for link-yoke 4-way control. The camera can be CMOS, CCD, or fiberscope. The LEDs can be replaced by fiber lighting.

Due to the unique scalability, efficient manufacturing, and a snap together assembly, the preferred link-yoke embodiment lends itself well for biometric applications utilizing AI.

The chain of links and yokes can be tailored to fit the anatomy of the patient at the most critical target area (142) where work is performed.

The length and diameter can be tailored to get over or through a restriction (308) in patient's body lumen or vessel. The distal link diameter of the articulated surgical device would be decreasing while proximal diameter is increasing. The larger proximal diameter is important to handling transmission of forces and resistance to buckling and twisting (stability) especially in a robotic system while applying work to a particular area.

As previously discussed, from historical biometric data, and data from the current pre-surgery patient CT or MM scans (FIG. 8, 200, 202), a 3D model of the pathway for a catheter procedure can be generated. After importing the 3D model into an AI software program (228) specifically engineered for biometric development of a catheter, the AI would determine the length and amount of taper necessary for matching to a patient's vessel in a particular procedure. The presently disclosed AI system can also consider robotic tracking, robotic motor loads and the design of the stepped transition along flexible links from the distal tip to the proximal end of the hyper flexibility portion of the catheter.

In a preferred embodiment, the presently disclosed AI system (228) will also generate the final design for a custom fitted articulated surgical device (catheter). The link lengths would be completely unique, cut from standard or custom diameter hypo-tube (220) as per FIG. 8. The yokes can be selectable from a group of non-transitioning (no step down) and transitioning (diameter step down) yokes.

In some embodiments, the AI system may start the design process at the target (142) in the 3D model and design the catheter from distal to proximal.

Other variables related to historical data and AI learning include:
1. Distance from lesion to robotic drive control head (tool coupling to robot)
2. Motor load output
3. Mid-line trajectory
4. Sharpest bend
5. Smallest vessel diameter along trajectory
6. Eccentric or concentric lesions
7. Restrictions
8. Pliability of vessel tissue/patient age/area of body
9. Therapy type
10. Lesion type, density, and hardness As previously discussed, FIGS. 10, 11, 12, and 13 show four pathway models. These models represent the inside of a body lumen, blood vessel, artery, or vein. There is a trajectory path (304) representing the theoretical path for the biometric catheter to follow. The lines perpendicular to the trajectory path (310) represent the diameter fiducials for the ideal clearance and fit of the articulated surgical device (catheter).

In some embodiments, the "design-AI" (FIG. 8, 228, FIG. 9) can analyze the 3D models from pre-CT/MRI scans and create a trajectory of the critical path with diameter fiducials in 3D. This approach can create the most efficient path from analyzing in-context data from potentially thousands of recorded procedures for a particular therapy. The in-context data can originally be created from manually driven surgical robots in record mode. As the history database becomes more complete (and the AI training matures) ideally this history database (training set) will have an extensive amount of information on the patients, their disease state, the procedure, and outcomes. Fitting the best trajectory is important, because this can be coupled to the delivery of a particular therapy.

In a preferred embodiment, the design-AI method (FIG. 8 228, FIG. 9) takes into consideration the stability needed for delivering a particular therapy from the articulated surgical device. The ability to build up the link-yoke catheter in ascending diameters from the target at the distal end to proximal helps to provide stability, control, and precision.

In some embodiments, the design-AI system (228, FIG. 9) can be configured to use a look up table to select known (e.g., commercially available) hypo-tube diameters (220). This allows the system to produce more manufacturable designs as it selects critical diameters to use in the appropriate sections with fiducials (see FIG. 14 and FIG. 15).

As previously discussed in FIGS. 10-15, the AI design system can generate diameter fiducials (e.g., reference points, fixed points, or lines) for a catheter that matches closely to the vessel's change in diameter and the type of distal tip necessary for working a particular lesion (target). In this case, the distal section is made smaller for the type of work. While moving proximally, the diameter steps up. In this case, it follows the natural taper of the vessel.

The AI software system (228) generates trajectory path and creates diameter fiducials and distances in between. This initial stick map can then convert to link length and yoke type (transition and non-transition).

For a sharp angle of attack, the AI system look at historical data for loads on robot motors and location of lesion. The distal section transitions from a small diameter capable of a tight bend radius to a large proximal diameter to stabilize and support the distal loads while work is being transmitted to the lesion.

As FIG. 10-13 shows, the AI software can generate diameter fiducials for a catheter that matches closely to the vessel's change in diameter and the type of distal tip necessary for working a particular lesion. In this case, the distal section is made smaller for the type of work. While moving proximally, the diameter steps up. In this case, it follows the natural taper of the vessel.

As per FIG. 13, for a restricted path, the AI can generate a necked down section to get beyond the restriction (308) and to the lesion location (142*c*). To apply stability to the catheter, the proximal section transitions rapidly to lager diameters. The AI would also use historical data from robotic motor loads to create the appropriate step up in transition from distal to proximal in the hyper flexible steering section of the catheter.

FIGS. 10 and 14 also show the design AI's implementation of the ideal position for the yoke pivots. Here, in some embodiments, after the trajectory path with diameter fiducials are mapped, the Design AI then locates the positions for the ideal yoke pivot (312).

In some embodiments, the design-AI system/method can take the trajectory paths and build a linear stick frame (FIG. 14 and FIG. 15) to determine the exact yoke pivot points (312) and build-length (314) for manufacturing. This provides the specification for manufacturing. The entire model of the assembly is built from this layout.

FIG. 14 shows that the design-AI system and method creates the linear layout of the stick frame showing yoke pivot points and diameter fiducials taken from the non-linear model of the patient's critical treatment zone. This simple layout gives the exact length and diameter of links and shows where pivots will be located.

FIG. 15 shows how the design-AI system and method can generate the envelope stick frame. This shows the envelope for which the link diameters and lengths follow. From this, an assembly can be automatically generated, followed by drawings and flat patterns for the laser cutting of the links.

Figure 16:
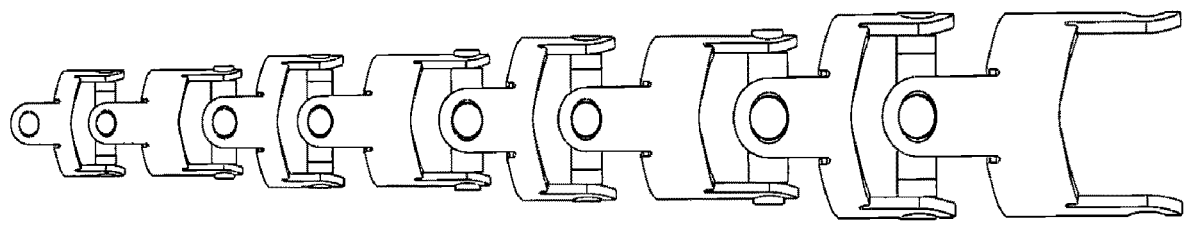
FIG. 16 shows a short, assembled section of the articulated surgical device, with the approximate lengths, diameters, and pivot points scaled roughly as shown in FIG. 14 and FIG. 15.

FIG. 16 shows a short section of the articulated surgical device, with the approximate lengths, diameters, and pivot points scaled roughly as shown in FIG. 14 and FIG. 15.

In some embodiments, as shown in FIG. 8, the design-AI builds the actual device assembly made from the selectable yokes and a selection of hypo-tube diameters. The link diameters can be chosen from standard or custom hypo-tube, using a look up table or other method. The length of the links can be variable, and each link can be serialized by the laser before dropping from the tube in the final cut, allowing each link to be directed to a particular assembly and patient. Therefore, the final inspection can be carried out by a visual robotic scanner, as desired.

The catheter is built up with an appropriate effector distal tip (based on therapy), the steering cables (112) are threaded through the yokes and the far proximal link is attached another tube section with suitable type of mobility or flexibility. The entire catheter is then encased in a biocompatible polymeric sheath (132) that allows for stretch and flexibility along with creating a smooth transitioning surface. This entire tube assembly is then connected to a drive cartridge (134) were the steering cables (112) from the link/yoke and potentially other more proximal independently steerable portions are fastened to the actuator spools or linear drives. This cartridge can be snapped into the articulated surgical device, forming a type of robot catheter where the cables (112) are activated based on input from a doctor or an autonomous AI controller.

The invention claimed is:

1. A computerized method of manufacturing an articulated surgical device, said method comprising:
receiving, into computer memory, surgical device pathway data describing one or more structural dimensions of a patient's body lumen or other internal body passage;
receiving into computer memory, target location data describing at least one target location in said patient's body, and its location relative to said surgical device pathway data;
receiving, into computer memory, articulated surgical device design parameters, said articulated surgical device comprising a plurality of connected units, one or more of said units having any of variable diameters and lengths;
said plurality of said units further comprising at least one movable joint, and configured to move about at least one axis;
using at least one computer processor, said surgical device pathway data, at least one said target location data, and said articulated surgical device design parameters to automatically design a patient customized articulated surgical device configured to traverse a pathway between an entry point on said patient's body lumen or other internal body passage, along said patient's body lumen or other internal body passage, and to said at least one target location; and
using said design to automatically fabricate at least portions of said articulated device.

2. The method of claim 1, wherein said surgical pathway data comprises at least one 3D image obtained from imaging scans of said patient;
said target location data comprises a location in said patient's body that can be accessed by traversing said body lumen or other internal body passage.

3. The method of claim 1, wherein said at least one computer processor automatically considers a plurality of alternate candidate articulated surgical device designs, and for one or more of said designs:
calculates a plurality of different paths that a given candidate articulated surgical device may traverse along said pathway between said entry point and said target; and
for one or more of said candidate articulated surgical devices, said at least one computer processor further considers the diameters of said given candidate articulated surgical device along said pathway, the ability of one or more of said units of said given candidate articulated surgical device to bend along said pathway, and an ability of one or more proximal units of said given candidate articulated surgical device to drive and/or guide distal units of said given candidate articulated surgical device as said distal units approach said target; and
said at least one computer processor preferentially selects those designs that meet preset criteria; said preset criteria comprising minimizing calculated trauma to any sides of said pathway between said entry point and said target.

4. The method of claim 3, wherein said ability of one or more proximal units of said given candidate articulated surgical device to drive and/or guide distal units of said given candidate articulated surgical device as said distal units approach said target comprise at least one of:
a) distance from said target to any proximal end motorized drive control head;
b) output of any motor used to drive a proximal end of said candidate articulate surgical device;
c) estimated mid-line trajectory of said candidate articulated surgical device as it transits a distance along said pathway from said entry point to said target;
d) estimated sharpest bend of said candidate articulated surgical device as it transits a distance along said pathway from said entry point to said target;
e) a smallest vessel diameter along a trajectory along said pathway between said entry point to said target location;
f) dimensions and characteristics of body lesions or abnormalities present at said target location;

g) restrictions along said pathway between said entry point to said target with a potential of impeding passage of said candidate articulate surgical device;

h) estimated pliability of any sides of said pathway between said entry point and said target;

i) type of therapy projected to be applied at said target.

5. The method of claim 3, wherein said at least one processor implements said automatic considerations by any of artificial intelligence type machine learning or a predetermined computer algorithm.

6. The method of claim 1, wherein said automatic fabrication comprises generating instructions to operate any of a CNC machining, or CNC laser cutting, or 3D printing device.

7. The method of claim 6, wherein said automatic fabrication further comprises using said instructions to operate any of a CNC machining, CNC laser cutting, or 3D printing device, thereby producing unit portions comprising at least portions of said units; and assembling said unit portions into at least portions of said articulated surgical device.

8. The method of claim 7, wherein said CNC machining, CNC laser cutting, or 3D printing device further uses at least one hypodermic tube as a starting material to produce said unit portions.

9. The method of claim 1, wherein said design further comprises units of varying lengths and diameters, such that the diameters of said units on a proximal side of said articulated surgical device are greater than the diameters of said units on a distal side of said articulated surgical device; and said lengths said units on a proximal side of said articulated surgical device are greater than the lengths of said units on a distal side of said articulated surgical device.

10. The method of claim 1, further covering at least portions of said articulated device with a flexible covering; said covering comprising a biocompatible polymer selected to reduce interaction between said articulated device and any of patient body fluids and/or non-target sides of said body lumen or other internal body passage; and/or wherein the interior of said articulated device is configured with a working channel with dimensions selected to enable one or more tools to traverse said working channel from an entry point to a most distal unit of said articulated device.

11. The method of claim 1, wherein one or more of said units are hypermobile units that further comprise at least two movable joints, and are configured to move about at least two axes;

wherein said hypermobile units further comprise a hypermobile link and a hypermobile joint, and one or more of said hypermobile joints further comprise:

a yoke comprising a polygonal or circumferential base, forming a central opening and having four vertically oriented pull wire holes disposed at ninety-degree intervals from one another; and four cylindrical pivot bosses extending laterally from said base at ninety-degree intervals;

said yoke configured to couple with a first link from its unit, and a second link from a neighboring unit;

said first link movably coupled with a first set of two of said four cylindrical pivot bosses and extending from said yoke in a first direction, such that said first link pivots in a first plane relative to said yoke; and said second link movably coupled with a second set of two of said four cylindrical pivot bosses and extending from said yoke in a second direction, such that said second link pivots in a second plane orthogonal to the first plane.

12. The method of claim 11, wherein said first link comprises:

a first ring;

a first set of arms extending vertically from said first ring in a first direction; and a second set of arms extending vertically from said first ring in a second, opposite direction; and said second link comprises;

a second ring;

a third set of arms extending vertically from said second ring in a first direction; and a fourth set of arms extending vertically from said second ring in a second, opposite direction;

and wherein each arm of the sets of arms comprises a circular hole sized to fit over one of the four cylindrical pivot bosses of said yoke.

13. The method of claim 11, wherein said bases of one or more of said yokes further comprise four vertically oriented pull wire holes disposed at ninety-degree intervals from one another, and wherein a plurality of said bases of said yokes of said articulated surgical device further comprises four pull wires disposed individually in each of said four pull wire holes.

14. The method of claim 11, wherein said design further comprises links and yokes of varying lengths and diameters, such that the diameters of said links and yokes on a proximal side of said articulated surgical device are greater than the diameters of said links and yokes on a distal side of said articulated surgical device; and said lengths of any of said set of arms on a proximal side of said articulated surgical device are greater than the lengths of said set of arms on a distal side of said articulated surgical device.

15. The method of claim 1, further attaching at least one effector unit comprising any of a camera, grasping tool, cutting tool, monopolar or bipolar electrodes, tissue sampling device, radioactive seed, or radiation or drug administration device to a most distal unit of said articulated surgical device.

16. A computerized system configured to manufacture articulated surgical devices, said system comprising:

At least one computer processor and computer memory, said computer memory comprising surgical device pathway data describing one or more structural dimensions of a patient's body lumen or other internal body passage;

said computer memory also comprising target location data describing at least one target location in said patient's body, and its location relative to said surgical device pathway data;

said computer memory also comprising articulated surgical device design parameters, said articulated surgical device comprising a plurality of connected units, one or more of said units having any of variable diameters and lengths;

said plurality of said units further comprising at least one movable joint, and configured to move about at least one axis;

said at least one computer processor configured to use said surgical device pathway data, at least one said target location data, and said articulated surgical device design parameters to automatically design a patient customized articulated surgical device configured to traverse a pathway between an entry point on said patient's body lumen or other internal body passage, along said patient's body lumen or other internal body passage, and to said at least one target location;

wherein said system further comprises automatic fabrication equipment configured to use said design to automatically fabricate at least portions of said articulated device.

17. The system of claim 16, wherein said at least one computer processor is configured to automatically evaluate a plurality of alternate candidate articulated surgical device designs, and for one or more of said designs:

said at least one computer processor is configured to calculate a plurality of different paths that a given candidate articulated surgical device may traverse along said pathway between said entry point and said target; and for one or more of said candidate articulated surgical devices, said at least one computer processor further evaluates the diameters of said given candidate articulated surgical device along said pathway, the ability of one or more of said units of said given candidate articulated surgical device to bend along said pathway, and an ability of one or more proximal units of said given candidate articulated surgical device to drive and/or guide distal units of said given candidate articulated surgical device as said distal units approach said target; and said at least one computer processor is configured to preferentially select those designs that meet preset criteria; said preset criteria comprising minimizing calculated trauma to any sides of said pathway between said entry point and said target.

18. The system of claim 17, wherein said at least one processor is configured to implement said automatic evaluations by any of artificial intelligence type machine learning or a predetermined computer algorithm.

19. The system of claim 16, wherein said automatic fabrication equipment is configured to receive instructions to operate any of a CNC machining, or CNC laser cutting, or 3D printing device; and wherein said automatic fabrication equipment further comprises any of a CNC machining, CNC laser cutting, or 3D printing device configured to producing unit portions comprising at least portions of said units.

20. The system of claim 16, wherein one or more of said units are hypermobile units that further comprise at least two movable joints, and are configured to move about at least two axes;

wherein said hypermobile units further comprise a hypermobile link and a hypermobile joint, and one or more of said hypermobile joints further comprise:

a yoke comprising a polygonal or circumferential base, forming a central opening and having four vertically oriented pull wire holes disposed at ninety-degree intervals from one another; and four cylindrical pivot bosses extending laterally from said base at ninety-degree intervals;

said yoke configured to couple with a first link from its unit, and a second link from a neighboring unit;

said first link movably coupled with a first set of two of said four cylindrical pivot bosses and extending from said yoke in a first direction, such that said first link pivots in a first plane relative to said yoke; and said second link movably coupled with a second set of two of said four cylindrical pivot bosses and extending from said yoke in a second direction, such that said second link pivots in a second plane orthogonal to the first plane.

\* \* \* \* \*